United States Patent
Cabilly et al.

[11] Patent Number: 5,865,974
[45] Date of Patent: *Feb. 2, 1999

[54] APPARATUS AND METHOD FOR ELECTROPHORESIS

[75] Inventors: Shmuel Cabilly, Gedera; Uri Yogev, Herzlia, both of Israel

[73] Assignee: Ethrog Biotechnology Ltd., Ganot, Israel

[*] Notice: The term of this patent shall not extend beyond the expiration date of Pat. No. 5,582,702.

[21] Appl. No.: 639,869

[22] Filed: Apr. 26, 1996

Related U.S. Application Data

[63] Continuation-in-part of Ser. No. 427,917, Apr. 26, 1995, Pat. No. 5,582,702.

[51] Int. Cl.⁶ .................................................. G01N 27/26
[52] U.S. Cl. ..................... 204/456; 204/606; 204/612; 204/615; 204/621
[58] Field of Search ...................... 204/450, 456, 204/606, 612, 615, 621

[56] References Cited

U.S. PATENT DOCUMENTS

| | | | |
|---|---|---|---|
| 3,715,295 | 2/1973 | Tocci | 204/456 |
| 4,323,439 | 4/1982 | O'Farrell | 204/180 |
| 4,874,491 | 10/1989 | Stalberg | 204/182.8 |
| 4,892,639 | 1/1990 | Sarrine et al. | 204/299 |
| 5,006,473 | 4/1991 | Bouma et al. | 436/516 |
| 5,045,164 | 9/1991 | Tansamrit et al. | 204/182.8 |
| 5,209,831 | 5/1993 | MacConnell | 204/299 R |
| 5,407,552 | 4/1995 | Lebacq | 204/299 |
| 5,411,657 | 5/1995 | Leka | 204/299 |
| 5,582,702 | 12/1996 | Cabilly et al. | 204/456 |

FOREIGN PATENT DOCUMENTS

WO 87/04948  8/1987  WIPO.

*Primary Examiner*—Kathryn Gorgos
*Assistant Examiner*—Edna Wong
*Attorney, Agent, or Firm*—Skjerven, Morrill, MacPherson, Franklin & Friel LLP

[57] ABSTRACT

A substantially closed cassette for conducting therein electrophoresis separation which includes a closed chamber, the chamber includes therein a body of gel, at least one ion source having a volume smaller than the volume of the gel for providing ions for driving the electrophoresis separation and electrodes for connecting the cassette to an external electrical power source, thereby enabling to drive the electrophoresis separation.

41 Claims, 8 Drawing Sheets

APPARATUS AND METHOD FOR ELECTROPHORESIS

CROSS REFERENCE TO OTHER APPLICATIONS

This application is a continuation in part application of U.S. Ser. No. 08/427,917 filed 26 Apr., 1995 now U.S. Pat. No. 5,582,702.

FIELD OF THE INVENTION

The present invention relates to electrophoresis generally and more particularly to apparatus for conducting an electrophoresis test therein.

BACKGROUND OF THE INVENTION

A great deal of diagnostic procedures and laboratory research are carried out wherein deoxyribonuveic acid (DNA), ribonuveic acid (RNA) or proteins are separated according to their physical and chemical properties via electrophoresis. This process is widely used and has many applications. For example, it is used to analyze DNA molecules according to their resultant size after being digested by restriction enzymes. It is also used to analyze the products of a polymerase chain reaction (PCR).

Typically, electrophoresis separation is carried out in a separation medium, such as a gel of agarose or acrylamide or a combination of the two. Usually, agarose gels are cast in open trays and form a slab whereas acrylamide gels are cast between two glass plates.

In order to effect the electrophoretic separation, two opposite ends of the gels are exposed to an electrically conducting buffer which is connected by electrodes, typically carbon or platinum, to an electric power source. Once the electrical power source is switched on, the electric field forces negatively charged molecules to move towards the anode and positively charged molecules to move towards the cathode. One characteristic of conventional electrophoresis is the use of large volumes of buffer having a relatively low salt concentration to maintain the required electric field.

DNA is negatively charged and therefore, in the agarose or acrylamide gels which provide sieving action, DNA molecules move towards the anode at a rate which depends on their size, wherein the smaller the molecules the faster they move.

Typically, it is desirable to visualize and to document the results of the electrophoretic separation test. In electrophoretic separation of DNA molecules, this has been done by immersing the gel slab after the electrophoretic separation has been completed in a solution of a fluorescent compound which emits visible light when exposed to a ultra violet (UV) light. A widely used compound is ethidium bromide.

Conventional electrophoretic separation systems are deficient in many respects, a few of which are listed below.

Prior art electrophoresis separation systems are a potential source of contamination to the working environment in which the tests are performed. The two major sources of contamination are ethidium bromide and PCR products. Ethidium bromide is a hazardous chemical due to its mutagenic activity and therefore, exposure to ethidium bromide may induce malignant tumors. PCR is an extremely sensitive method to the extent that a single molecule of DNA product from one PCR (out of the trillions of molecules being produced) may interfere with the subsequent PCR such that it will produce incorrect result.

Conventional electrophoresis is also deficient in other respects, one being that it is time consuming.

Various attempts have been made to solve the deficiencies of conventional electrophoresis. Most attempts have been addressed to overcome the deficiency of conventional electrophoresis systems with respect to the use of buffers therein.

U.S. Pat. No. 4,874,491 to Stalberg describes an electrophoresis system having a high concentration buffer containing gel.

U.S. Pat. No. 4,892,639 to Sarrine et al. describes an electrophoresis plate with improved buffer circulation.

U.S. Pat. No. 5,045,164 to Tansamrit et al. describes an electrophoresis plate having thickened ends as buffer reservoirs.

U.S. Pat. No. 5,209,831 to MacConnel describes a bufferless disposable cassette having open ends and conductive film electrodes.

SUMMARY OF THE INVENTION

It is therefore an object of the present invention to provide an improved apparatus for electrophoresis.

A major object of the present invention is to provide a closed cassette for electrophoresis which is substantially closed before, during and after an electrophoresis test conducted therein.

According to an aspect of the present invention the cassette is a disposable cassette.

The cassette of the present invention overcomes drawbacks associated with prior art electrophoresis cassettes, plates or slabs. Since the cassette is a closed one, its outer environment is not susceptible to contamination. Moreover, since it is ready to use, the preparation time required for preparing prior art cassettes is saved.

Another object of the present invention is to provide an electrophoresis system in which both the electrophoretic separation and the visualization of the results thereof are done while the cassette is in situ.

According to one aspect of the present invention, there is provided a substantially closed disposable cassette with openings for introducing a sample of molecules thereinto, the openings being preferably opened only just before the electrophoresis test.

According to another aspect of the present invention, the cassette includes all the chemical compounds required to drive the electrophoretic separation, and, when DNA molecules are separated, the compounds required to stain the separated DNA.

According to yet another aspect of the invention, the volume of the ion source utilized for providing the ions required for the electrophoresis separation is smaller than the volume of the gel utilized as the electrophoresis separation matrix and preferably smaller than the volume of gel utilized for actual separation during an electrophoresis test.

According to a preferred embodiment of the present invention, the ions (cations and anions) required to drive the electrophoretic separation are provided by a cation exchange matrix and an anion exchange matrix, respectively.

According to another preferred embodiment of the present invention, the cation exchange matrix also provides the cations required to stain the separated molecules in order to enable visualization thereof when the cassette is illuminated with a UV light source.

According to an alternative embodiment of the present invention the ions required to drive the electrophoresis separation are provided by a reservoir, preferably a breakable ampoule containing a buffer characterized by relatively high concentration of these ions.

One advantage of the cassette of the present invention is that it is disposable.

Another advantage of the cassette of the present invention is that the user is not exposed to any hazardous chemical constituent, such as ethidium bromide, as in prior art cassettes.

Yet another advantage of the cassette of the present invention is that PCR-DNA products are contained within the cassette and are disposed therewith so as to substantially reduce the contamination of the working environment in which the tests are performed.

There is thus provided, in accordance with a preferred embodiment of the present invention, an apparatus for conducting electrophoresis separation therein which includes a housing having at least bottom and side walls defining a chamber, wherein the chamber includes in contact therebetween a body of gel for carrying therein the electrophoresis separation, at least one ion source for providing ions for driving the electrophoresis, the at least one ion source having a volume smaller than the volume of the body of gel, and electrodes for connecting the chamber to an external electrical power source, thereby enabling to drive the electrophoresis separation.

There is also provided, in accordance with a preferred embodiment of the present invention a substantially closed cassette for conducting therein electrophoresis separation which includes a closed chamber which includes therein a body of gel for carrying therein the electrophoresis separation, at least one ion source for providing ions for driving the electrophoresis separation, and electrodes for connecting the cassette to an external electrical power source, thereby enabling to drive the electrophoresis separation.

According to a preferred embodiment, the volume of the at least one ion source is smaller than the volume of the body of gel utilized in the electrophoresis separation.

In a preferred embodiment, the at least one ion source includes a body of ion exchange matrix. Further, the body of ion exchange matrix includes a body of cation exchange matrix for providing the cations for driving the electrophoresis separation and a body of anion exchange matrix for providing the anions for driving the electrophoresis separation. Still further, the cation exchange matrix is disposed at one end of the body of separating gel and the body of anion exchange matrix is disposed on a second end of the separating gel.

In operation, the cation exchange matrix exchanges protons derived from electrolysis with the cations for driving the electrophoretic separation and the anion exchange matrix exchanges hydroxyl ions derived from the electrolysis with the anions for driving the electrophoretic separation.

According to a preferred embodiment of the present invention, the cation exchange matrix and the anion exchange matrix includes particles immersed in a support matrix. Preferably, the support matrix is formed of the gel as the body of gel for carrying the electrophoresis separation therein.

In accordance with yet a further embodiment of the present invention, the apparatus also include an additional body of gel of low gel strength disposed between the side wall of the chamber and the anion exchange matrix, the body of gel of low gel strength shrinking during the electrophoresis separation, thereby providing a volume in which gases produced at the vicinity of an anode of the chamber accumulates.

Further, according to a preferred embodiment of the present invention, the apparatus includes a buffer solution in contact with the body of separating gel, the at least one body of ion exchange matrix and the electrodes. Preferably, the buffer is a tris-acetate (TAE) buffer, thus the cation exchange matrix releases Tris cations and the anion exchange matrix releases acetate anions.

Additionally, according to a preferred embodiment of the present invention, the cation exchange matrix includes ethidium cations.

In accordance with an alternative embodiment of the present invention, the least one ion source includes a closed reservoir having therein a buffer solution having higher concentration than a concentration of a buffer solution of the body of gel for carrying therein the electrophoresis separation, the closed reservoir being opened just before the electrophoresis separation for providing the ions for driving the electrophoresis separation.

In a preferred embodiment, the closed reservoir is a breakable ampoule. Further, the breakable ampoule may be surrounded by a space, the space at least partially filled with the buffer solution in a concentration generally similar to that of the body of gel for carrying therein the electrophoresis separation. Preferably, the buffer is a TAE buffer. In addition, the buffer may also include ethidium cations.

The apparatus and cassette of the present invention are further characterized by any combination of the following features:

The chamber or the cover may include at least one opening therein for introducing at least one test sample into the body of gel. Preferably, the at least one opening is closed by a comb prior to the electrophoresis separation.

The chamber and/or the cover may be transparent to ultra violet (UV) radiation.

The chamber or cover may also include at least one vent hole which is closed prior to the electrophoresis test and is being opened just before the electrophoresis test.

Further, according to a preferred embodiment of the present invention, the electrodes include a conductive material capable of adsorbing at least part of at least one of the gases produced during the electrophoresis separation. Preferably, the at least one electrode capable of adsorbing is substantially formed from a material selected from the group consisting of aluminum and palladium.

Additionally, the gases include oxygen created at the vicinity of the anode during the electrophoresis separation and reacting with the aluminum. Alternatively, the gases include hydrogen created at the vicinity of the cathode during the electrophoresis separation and wherein the hydrogen is adsorbed by the palladium.

In an alternative embodiment, the at least one electrodes includes a strip of conductive material. Preferably, the strip of conductive material is mounted on a ramp, the ramp being inclined at an angle relative to the bottom wall, whereby gases produced at the vicinity of the strip during the electrophoresis separation are being directed to an empty volume receiving the gases.

Finally, the apparatus or cassette may also include at least one empty volume for accumulating gases produced during the electrophoresis test.

There is also provided, in accordance to a preferred embodiment of the present invention a system for conducting electrophoresis separation which includes an electrical power source, a substantially closed disposable cassette, preferably, but not necessarily the apparatus or cassette of the present invention, and a support for supporting the substantially closed cassette and for connecting the electrical power source to the conductive elements of the cassette.

Further, the system may also include a UV light source and wherein the cassette is transparent to UV light, and wherein the cassette also includes a UV sensitive material capable of interacting with the molecules undergoing electrophoresis separation and of emitting light, thereby enabling to conduct the electrophoresis separation and to visualize it while the cassette is in situ. In a preferred embodiment, the UV sensitive material is ethidium bromide.

Still further, the system may also include camera means for documenting the results of the electrophoresis separation. The system may also include a computer which includes at least one image analysis application for analyzing the results of the electrophoresis separation.

Additionally, the system may include a cooling system for cooling the cassette during the electrophoresis test.

There is also provided, in accordance with a preferred embodiment of the present invention, an electrophoresis method which includes the steps of introducing at least one test sample into a body of gel, applying an electrical field to the body of gel and driving an electrophoresis separation by providing ions required for driving the electrophoresis separation by at least one ion source having a volume smaller than the volume of the gel.

Finally, there is also provided, in accordance with a preferred embodiment of the present invention, a method for producing a substantially closed cassette for conducting electrophoresis separation therein which includes the steps of providing a housing having bottom and side walls defining an open chamber, assembling within the chamber in contact therebetween a body of gel for carrying therein the electrophoresis separation, at least one ion source for providing ions for driving the electrophoresis separation, the at least one ion source having a volume smaller than that of the body of gel and electrodes for connecting the chamber to an external electrical power source, and closing the open housing with a cover, thereby forming a substantially closed cassette capable of carrying the electrophoresis separation therein.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Reference is now made to FIGS. 1–4 which illustrate an electrophoresis disposable cassette, generally referenced 10, constructed and operative in accordance with a preferred embodiment of the present invention.

Figure 1:
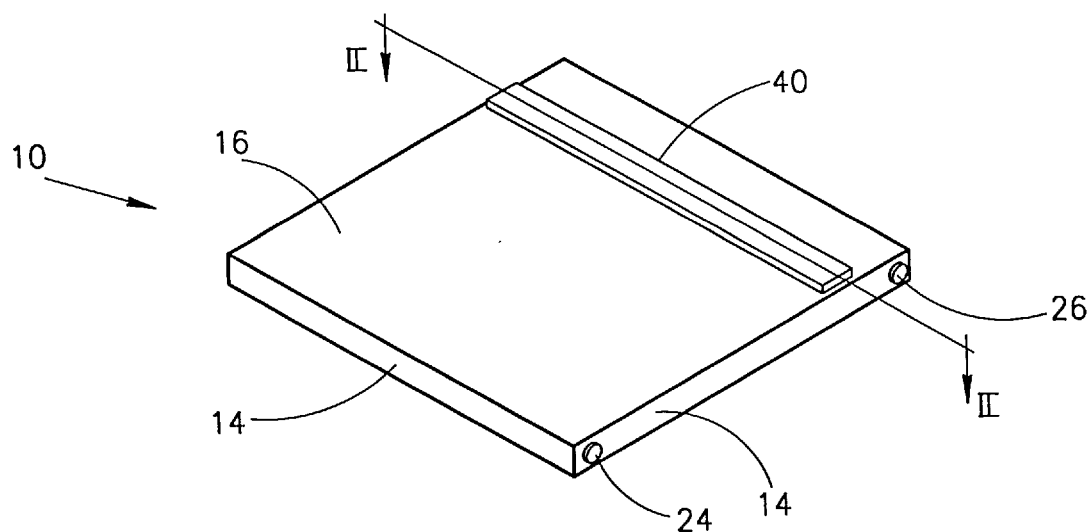
FIG. 1 is a schematic isometric illustration of an electrophoresis cassette, constructed and operative in accordance with a preferred embodiment of the present invention.

Cassette 10, as best seen in FIG. 1, is a closed disposable cassette preferably, but not necessarily, used for a single electrophoresis test. Cassette 10 includes all the chemical compounds required for driving the electrophoresis separation and for enabling visualization of its results when DNA as well as RNA or protein molecules have been separated.

Figure 3:
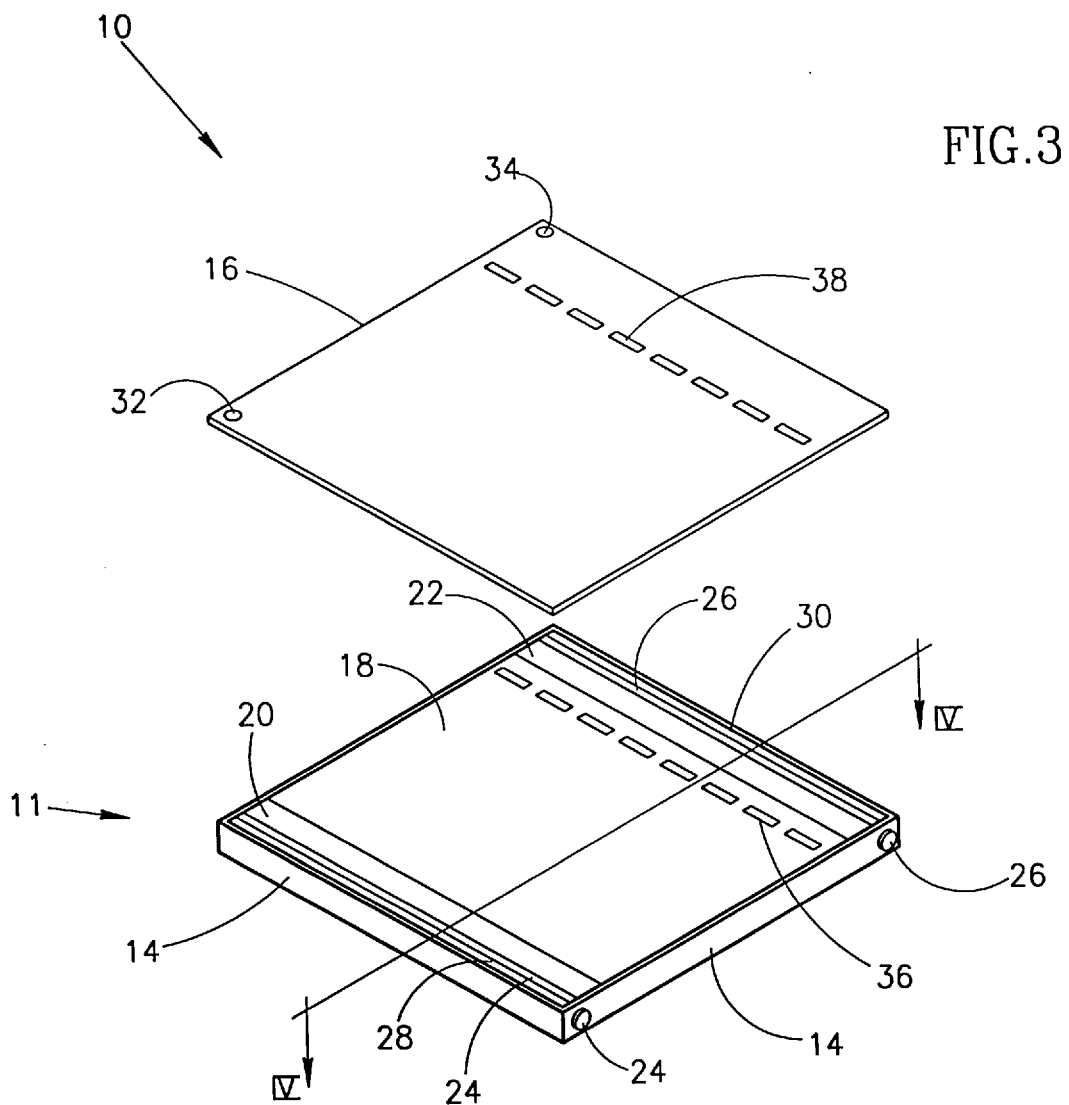
FIG. 3 is a schematic isometric exploded illustration of the electrophoresis cassette of FIG. 1.

As best seen in FIG. 3, the cassette 10 preferably comprises a three dimensional chamber 11 which is preferably substantially flat, having bottom wall and side walls, referenced 12 and 14 respectively, and a cover 16 which forms the top wall of the cassette. The bottom wall 12 (FIG. 4) and the cover 16 are preferably made of any suitable UV transparent material, such as the TPX plastic commercially available from MITSUI of Japan or the PMMA plastic, commercially available from Repsol Polivar S.P.A. of Rome. In a preferred method for producing cassette 10 a plastic molding process is employed utilizing a Rohaglas Molding Powder, commercially available from Sidas GmbH of Damstadt, Germany.

Figure 4:
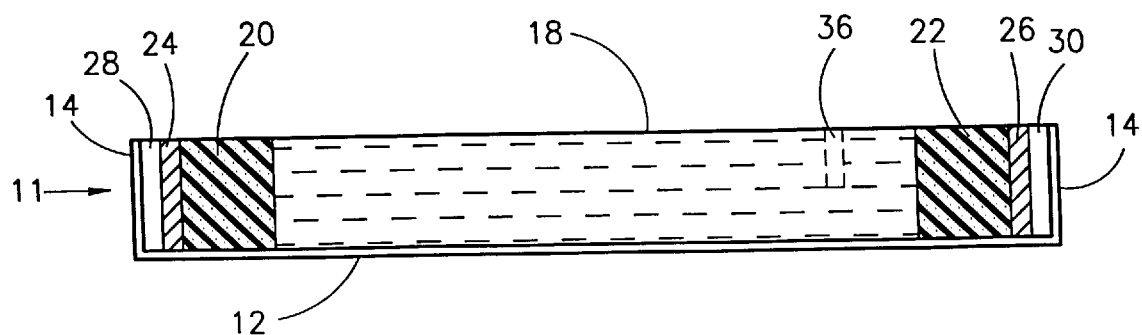
FIG. 4 is a schematic cross section illustration along lines IV—IV in FIG. 3.

As best seen in the cross section illustration of FIG. 4, chamber 11 preferably comprises a gel matrix 18 which may be any suitable gel matrix for electrophoresis, such as an agarose gel or a gel made of acrylamide, a cation exchange matrix 20 and an anion exchange matrix 22, collectively referred to as the ion exchange matrices 20 and 22. Chamber 11 further comprises two conductive rods referenced 24 and 26, such as stainless steel rods which, when connected to an external direct current (DC) electrical power source, provide the electric field required to drive electrophoretic separation. In the illustrated embodiment, rod 24 is the anode and rod 26 is the cathode. Chamber 11 further comprises two empty volumes 28 and 30, in which gases produced during the electrophoresis test may accumulate. Alternatively, the open cover 16 may include two vent holes 32 and 34, shown only in FIG. 3, for venting the gases accumulated in the empty volumes 28 and 30.

A particular feature of cassette 10, as best shown in FIGS. 3 and 4 is that the volume of the ion source, the ion exchange matrices 20 and 22 in the illustrated embodiment, is smaller than the volume of the gel 18 utilized as the electrophoresis separation matrix and preferably smaller than the volume of gel utilized for actual separation during an electrophoresis test.

It will be appreciated that if cassette 10 includes vent holes 32 and 34 they are sealed prior to the beginning of the electrophoretic test, and are opened just before the electrophoresis test begins and are closed again after the test is completed to substantially reduce the possibility of contamination originated therefrom.

Preferably, each of the gel 18, the ion exchange matrices 20 and 22 and the conductive rods 24 and 26 are in contact and are immersed in a relatively small amount of an agarose matrix produced and including a buffer solution, such as a TAE buffer, which facilitates the mobility of the molecules undergoing separation and of the ions provided by the ion exchange matrices 20 and 22.

It is a particular feature of the present invention that the ions required for driving the electrophoretic separation are provided by the ion exchange matrices 20 and 22, preferably, by exchanging with protons and hydroxyl ions derived from electrolysis of $H_2O$. In operation, a DC current is applied via rods 24 and 26 to initiate the electrolysis which in turn initiates the operation of the ion exchange matrices.

The cation exchange matrix 20 and the anions exchange matrix 22 release the cations and anions required for driving electrophoresis separation. An example of a suitable cation is the $Tris^{(+)}$ cation and an example of a suitable anion is $acetate^{(-)}$. Preferably, but not necessarily, the ions released by the ion exchange matrices 20 and 22 are exchanged with adsorbed protons and hydroxyl anions, respectively. Alternatively, or in addition thereto, the ions adsorbed by the ion exchange matrices 20 and 22 may also be provided by the rods 24 and 26.

It will be appreciated that the use of the ion exchange matrices 20 and 22 provides a generally uniform pH throughout the cell since any proton buildup near the anode 24 is compensated by absorption thereof by the neighboring cation exchange matrix 20 and hydroxyl buildup near the cathode 26 is compensated by absorption thereof by the anion exchange matrix 22.

According to one preferred embodiment of the present invention, the cation exchange matrix 20 and the anions exchange matrix 22 may be immersed in one of the materials used for preparing the gel.

A suitable cation exchange material is the CM-25-120 Sephadex and suitable anion exchange materials are the WA-30 and the A-25-120, all of which are commercially available from Sigma Inc. of St. Louis, U.S.A.

Cassette 10 preferably also includes wells 36 in the gel 18. Wells 36 are used to introduce samples of the molecules which are to undergo electrophoretic separation. The wells 36 may be formed by any suitable method, such as by introducing a comb like structure 40 (FIG. 2) to the gel during the assembly of the gel. The comb 40 is introduced to the gel via corresponding openings 38 (FIG. 1) in the cover 16. The openings 38 may be used as an additional space for loading the molecular samples just before the onset of the electrophoresis test after the comb 40 is removed.

Figure 2:
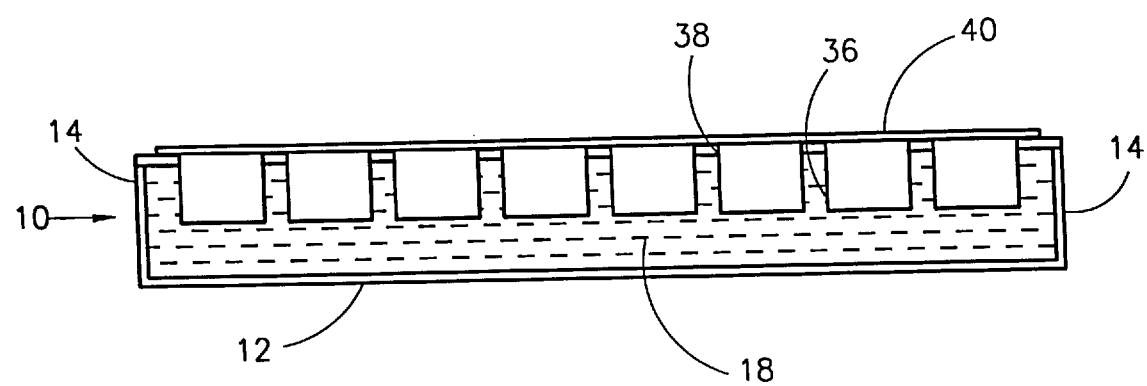
FIG. 2 is a schematic cross section illustration along lines II—II in FIG. 1.

According to a preferred embodiment of the present invention, as best seen from FIG. 2, the wells 36 are covered by the comb 40 used in their preparation. This is since the comb method involves insertion of a comb structure into the gel via the openings 38 in the top cover 16, the comb being pulled out only just before the electrophoresis test.

It is a particular feature of the present invention that the cassette 10 is a closed cassette covered by the comb 40 which is removed just before the electrophoresis test itself.

The cassette 10 also includes a source for ethidium cations which are used for ultra violet (UV) visualization of the separated DNA molecules. Unlike prior art electrophoresis systems, in which ethidium bromide is introduced after separation of the molecules, typically by immersing the gel in an ethidium bromide solution, the cassette 10 includes an internal source for ethidium ions source. Preferably, the cation exchange matrix 20 releases not only the TRIS cations but also ethidium cations which interact with the molecules undergoing electrophoretic separation.

In a preferred embodiment, the cation exchange matrix 20 provides a continuous flux of ethidium cations during the electrophoresis test so as to stain the DNA molecules so as to enable their visualization and analysis, in situ, utilizing a suitable electrophoresis system, such as the system described with reference to FIG. 16 hereinbelow.

The following examples, which are not intended to limit the scope of the present invention, illustrate how the cation exchange matrix 20 and the anion exchange matrix 22 are prepared. The following example is for a cassette whose outer length, width and height are 100 millimeters (mm), 80 mm and 6 mm, respectively. It will be appreciated that a cassette of these outer dimensions is substantially flat.

EXAMPLE 1

The cation exchange matrix 20 was prepared as follows:
A. About 5 grams of CM-25-120 Sephadex particles were washed using three volumes of TAE solution in a concentration 50 times higher than the concentration of the TAE buffer used during the electrophoresis test (herein X50 TAE solution). In this example, the concentration used in the electrophoresis test itself was 0.04 Molar of Tris Acetate with 0.002 Molar ethylenediamine tetra acetic acid (EDTA).
B. The CM-25-120 Sephadex particles were washed by distilled water.
C. Two grams of the washed CM-25-120 Sephadex particles were mixed with 50 ml 0.5× TAE buffer and 5 microliter of ethidium bromide.
D. The mixture was left without agitation for an hour so as to let the CM-25-120 particles to settle.
E. 25 ml of the mixture were filtered out so as to obtain a 25 ml solution including the 2 grams CM-25-120 Sephadex particles.
F. The obtained 25 ml mixture including the CM-25-120 Sephadex particles were immersed in a 4 percent agarose gel to obtain the cation exchange matrix 20.

The anion exchange matrix 22 is prepared as follows:
A. About 3 grams of WA-30 particles were washed using three volumes of the 50× solution used to wash the cation exchange particles.
B. The WA-30 particles were washed by distilled water.
C. One gram of the WA-30 particles was immersed in a 4 percent agarose gel to obtain the anion exchange matrix 22.

EXAMPLE 2

The cation exchange matrix 20 is prepared as follows:
A. 20 grams of swollen CM-25-120 Sephadex particles were placed in a standard column and washed with 500 ml of 1.2 Molar TAE solution, having a pH of 9.3 as adjusted with HCl.
B. The CM-25-120 Sephadex particles were washed with 7 volumes of distilled water.
C. The CM-25-120 Sephadex particles were removed from the column and kept in two volumes of 0.6× TAE buffer.

D. 1 ml of swollen CM-25-120 Sephadex were adsorbed with ethidium bromide to saturation and the Bromide ions were washed out.

E. 1.2 ml of the particles CM-25-120 kept in the TAE buffer (step C) and 3 microliter of the particles adsorbed with ethidium (step D) were immersed with 1.5 ml of 2% agarose gel which forms the agarose matrix to obtain the cation exchange matrix 20 for cassette 10.

The anion exchange matrix 22 was prepared as follows:

A. 25 grams of DEAE Sephadex A-25-120 particles were placed in a standard column and washed with 500 ml of 1 Molar sodium acetate solution of pH 7 adjusted with acetic acid.

B. The A-25-120 particles were washed with 7 volumes of distilled water.

C. The A-25-120 Sephadex particles were removed from the column and kept in two volumes of 0.6× TAE buffer.

D. 1.2 ml of the particles A-25-120 adsorbed with acetate ions (step C) were immersed with 1.5 ml of 2% agarose gel which forms the agarose matrix to obtain the anion exchange matrix 22 for cassette 10.

Figure 5:
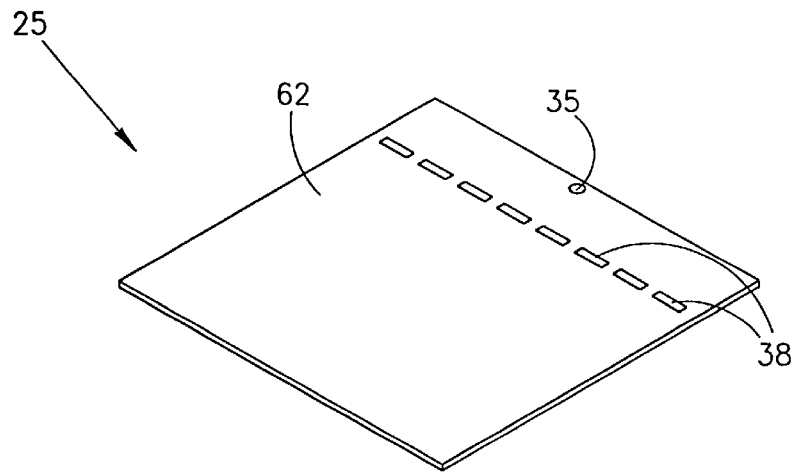
FIG. 5 is a schematic isometric exploded illustration of an electrophoresis cassette, constructed and operative in accordance with a second preferred embodiment of the present invention.
Figure 6:
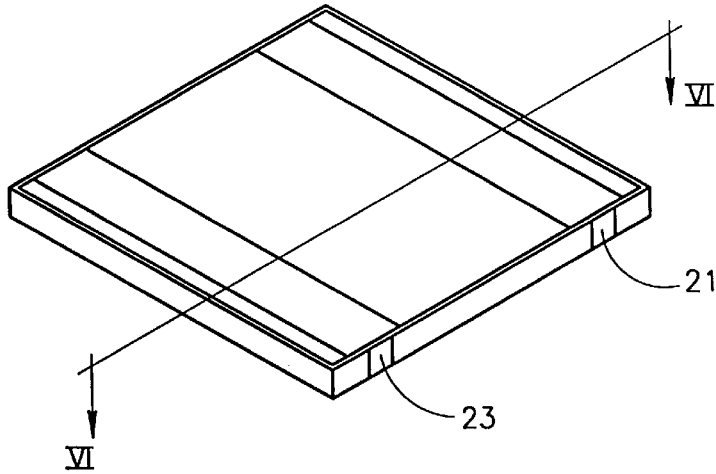
FIG. 6 is a schematic cross section illustration along lines VI—VI in FIG. 5.
Figure 6:
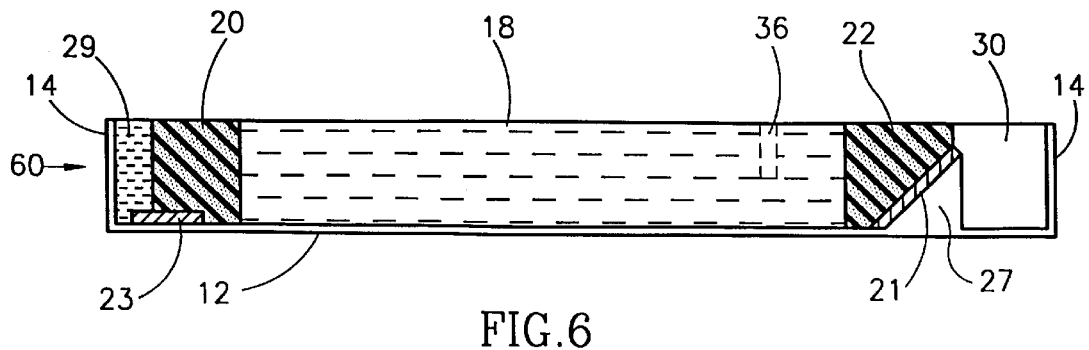
Figure 7:
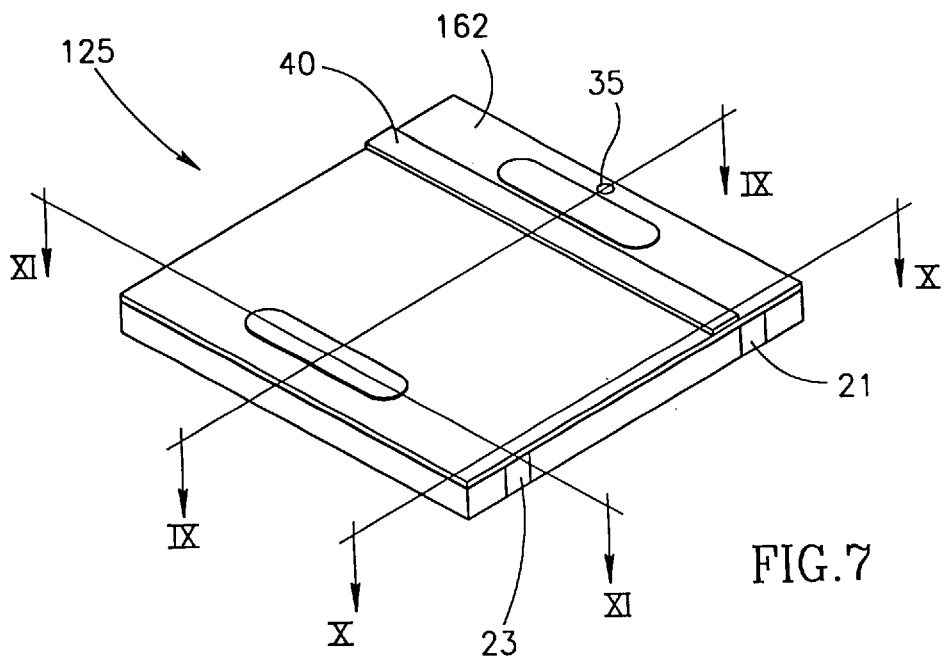
FIG. 7 is a schematic isometric illustration of an electrophoresis cassette, constructed and operative in accordance with a third preferred embodiment of the present invention.
Figure 8:
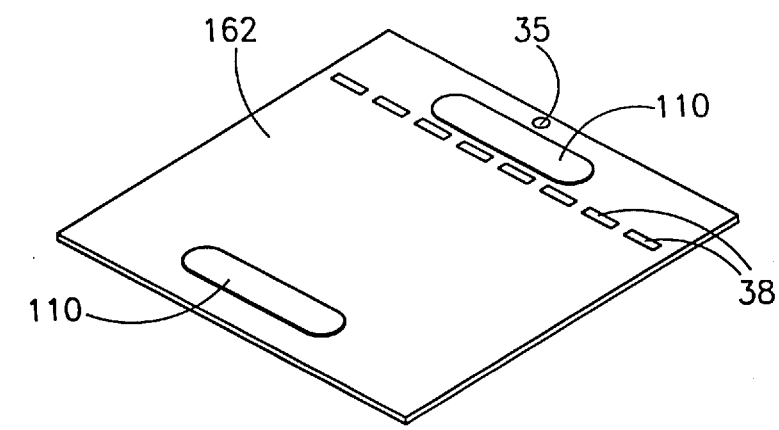
FIG. 8 is a schematic isometric exploded illustration of the electrophoresis cassette of FIG. 7.
Figure 8:
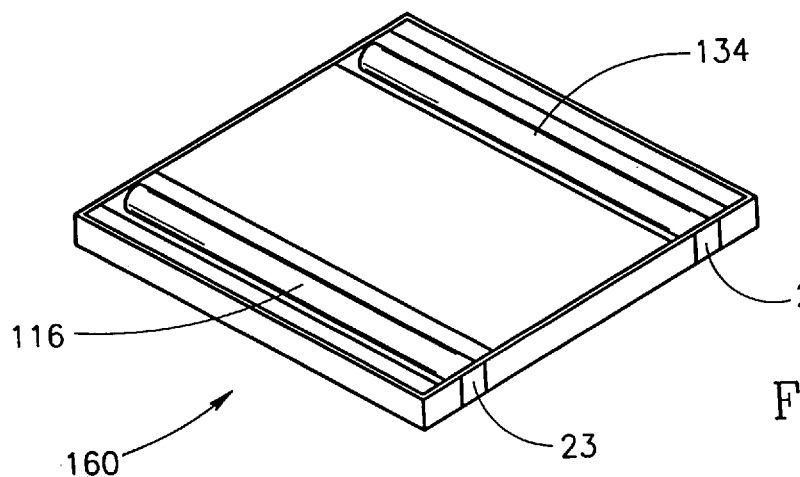
Figure 9:
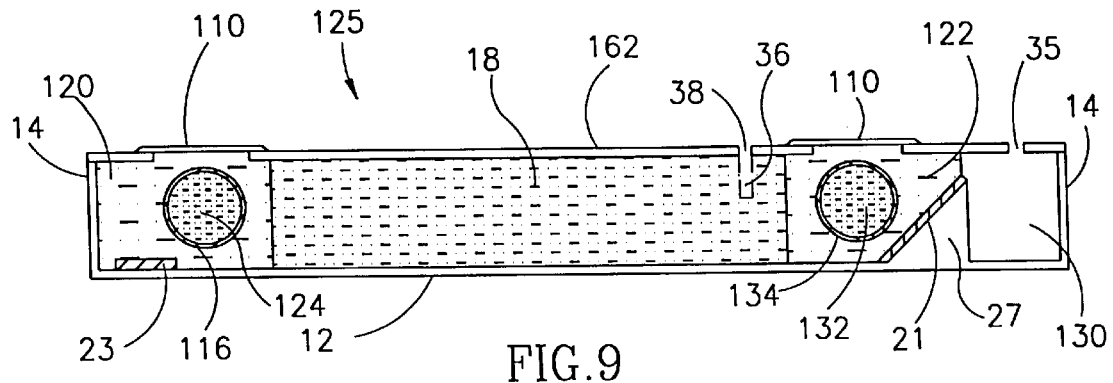
FIG. 9 is a schematic cross section illustration along lines IX—IX in FIG. 7.
Figure 10:
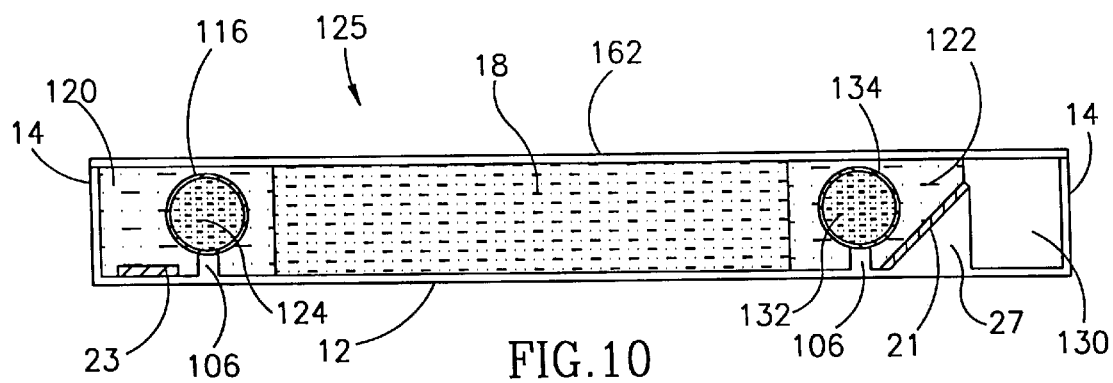
FIG. 10 is a schematic cross section illustration along lines X—X in FIG. 7.
Figure 11:
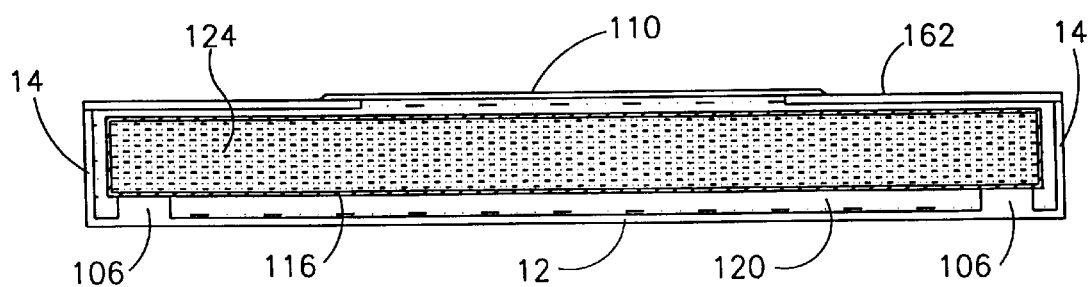
FIG. 11 is a schematic cross section illustration along lines XI—XI in FIG. 7.
Figure 12:
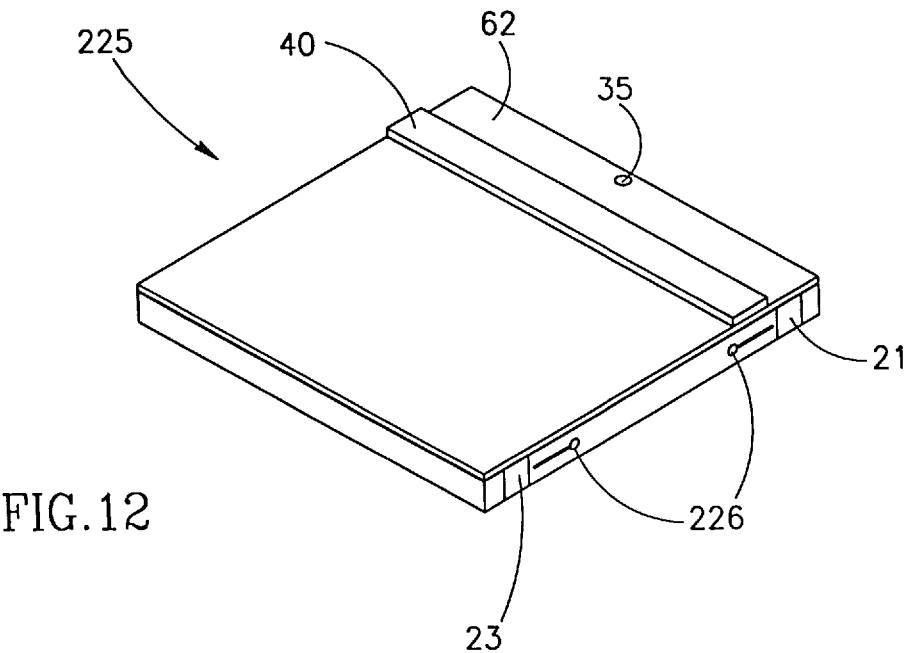
FIG. 12 is a schematic isometric illustration of an electrophoresis cassette, constructed and operative in accordance with a fourth preferred embodiment of the present invention.

Reference is now made to FIGS. 5 and 6 which illustrate an electrophoresis cassette, generally referenced 25, constructed and operative in accordance with a second preferred embodiment of the present invention.

Cassette 25 is generally similar in construction and operation to cassette 10 (FIGS. 1–4), i.e. it is a closed disposable cassette preferably used for a single electrophoresis test which comprises a gel 18 and an ion exchange matrices 20 and 22. Therefore similar elements of cassettes 10 and 25 are referenced by similar reference numerals (e.g. comb 40).

Chamber 60 comprises similar to chamber 11 a gel matrix 18 and an ion exchange matrices 20 and 22. However, chamber 60 differs from chamber 11 in construction and operation with respect to the anode and cathode and the gas accumulation and venting mechanism.

Chamber 60 comprises two conductive strips 21 and 23 which form the cathode and anode, respectively. Cathode 21 is diagonally supported by a diagonal ramp 27, ramp 27 preferably forms an integral part of chamber 60. Anode 23 is positioned under ion exchange matrix 20 and an additional gel matrix 29 which shrinks during electrophoresis due to electroendosmosis as described in detail hereinbelow. Gel matrix 29 is preferably the same gel as gel matrix 18, however its gel strength is lower than that of gel 18. For example, gel matrix 18 is comprised of 2% agarose while the gel matrix 29 comprises 0.3% agarose.

In operation, during an electrophoresis test, water flows from the anode side to the cathode side of the gel matrices due to electroendosmosis. Consequently, gel matrix 29 gradually shrinks, thereby creating a space in which gases generated in the vicinity of anode 23 accumulate.

According to a further preferred embodiment of the present invention, cathode 21 and anode 23 are made of a conductive material that is capable of adsorbing gases produced during the electrophoretic separation process.

In a preferred embodiment, cathode 21 and anode 23 are made of aluminum. During electrophoresis, the oxygen produced at the vicinity of anode 23 reacts with the aluminum anode to form aluminum oxide, whereby less free oxygen is produced at the anode side. The reduction in the volume of gas produced, together with the space created for gas accumulation by the shrinkage of gel matrix 29, alleviates the need for a vent hole in the anode side of cassette 25. Thus, cassette 25 may include in its cover 62 only a single vent hole 35 above empty volume 30 which is adjacent to the cathode.

In an alternative embodiment, the anode is made of aluminum as described hereinabove whereas the cathode is formed of palladium or any other suitable conductive material which adsorbs hydrogen at the cathode side.

Yet another particular feature of cassette 25 is that cathode 21 is diagonally supported by ramp 27. This facilitates continuous contact between the cathode and the surface of the anion exchange matrix 22 overlying cathode 21, whereby release of gas bubbles produced at the vicinity of cathode 21 are directed towards empty volume 30.

In a preferred embodiment, ramp 27 is formed as an integral part of chamber 60 and is inclined to the bottom wall 12 at an angle of about 45 degrees.

Reference is now made to FIGS. 7–11 which illustrate an electrophoresis cassette, generally referenced 125, constructed and operative in accordance with yet another preferred embodiment of the present invention. Cassette 125 similarly to cassettes 10 and 25 is a closed disposable cassette used for a single electrophoresis test and including all the chemical compounds required for driving the electrophoresis separation and for enabling visualization of its results when DNA as well as RNA or protein molecules have been separated.

Cassette 125 comprises a three dimensional chamber 160 generally similar to chamber 60 of cassette 25 and a cover 162 generally similar to cover 62 of cassette 25. Cassette 125 differs from cassette 25 in its ion source for driving the electrophoresis separation. In the illustrated embodiment, elements which are generally similar to elements of cassettes 10 and 25 are designated by similar reference numerals (e.g. gel 18).

In chamber 160, the body of gel 18 is disposed intermediate two spaces 120 and 122 containing a buffer solution, such as the TAE buffer solution described hereinabove. Each of volumes 120 and 122 comprises therein a closed reservoir which includes the same buffer however in a higher concentration so as to provide the ions for driving the electrophoresis separation. In the illustrated preferred embodiment, the closed reservoirs are breakable ampoules 116 and 134 including buffer solutions 124 and 132, respectively which are of higher concentration than that of volumes 120 and 122. As a non limiting example, the concentration of solutions 124 and 132 is fifty fold higher than that of the buffer solutions of spaces 120 and 122.

It will be appreciated that ampoules 116 and 134 are formed of any sealed suitable material impermeable to water, such as plastic or glass, thus the concentrated buffer solutions 124 and 132 therein are not in contact with the buffer solutions filling volumes 120 and 122.

In the illustrated embodiment ampoules 116 and 134 are supported by ampoule supports 106. In operation, the user breaks ampoules 116 and 134 so as to provide the ions in the high concentration buffers 124 and 132, respectively, in order to provide the ions required to run the electrophoresis test, preferably, after the DC current is provided to cassette 125.

In the illustrated embodiment, each of ampoules 116 and 134 is supported under a flexible cover 110. Flexible covers 110 are formed of any flexible material responsive to mechanical force, such as rubber, so as to enable breaking of ampoules 116 and 134 once pressure is applied thereon, thereby releasing their contents into buffer spaces 120 and 122 respectively.

Optionally, concentrated buffer solution 124 also contains a suitable material for DNA staining, preferably any source for ethidium cations, such as ethidium bromide so as to enable UV visualization of the separated DNA samples as described hereinabove. In this case, chamber 160 is formed of a UV transparent material.

Reference is now made to FIGS. 12–15 which illustrate an electrophoresis cassette, generally referenced 225, constructed and operative in accordance with yet another preferred embodiment of the present invention. Cassette 225 is similar to cassette 125 and similarly to cassettes 10 and 25 and 125 is a closed disposable cassette used for a single electrophoresis test and including all the chemical compounds required for driving the electrophoresis separation and for enabling visualization of its results when DNA as well as RNA or protein molecules have been separated.

Cassette 225 is generally similar to cassette 125 in construction and operation and similar elements are referenced by similar reference numerals. Cassette 225 differs from cassette 125 in its ampoule and its mechanism for breaking it.

Figure 13:
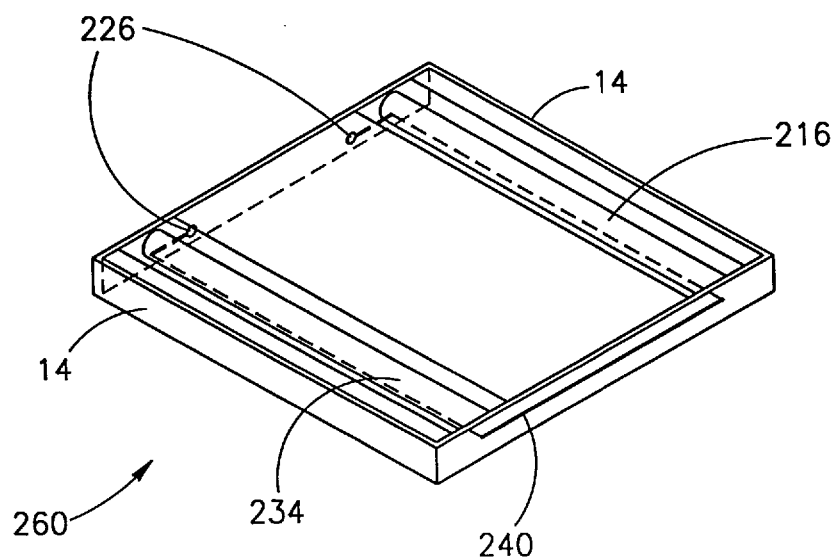
FIG. 13 is a bottom up cut away schematic isometric illustration of the electrophoresis cassette of FIG. 12.
Figure 14:
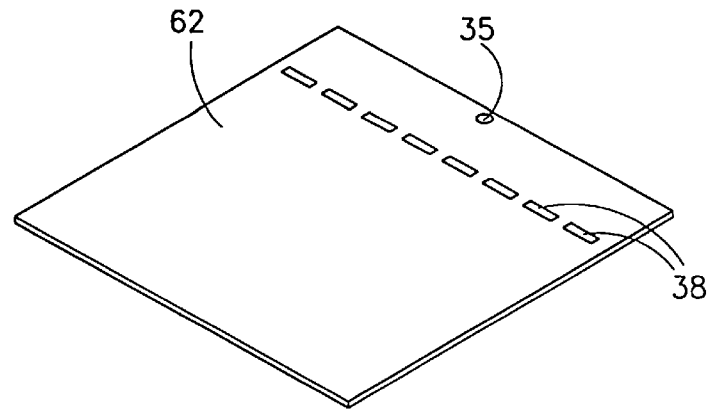
FIG. 14 is a schematic isometric exploded illustration of the electrophoresis cassette of FIG. 12.
Figure 15:
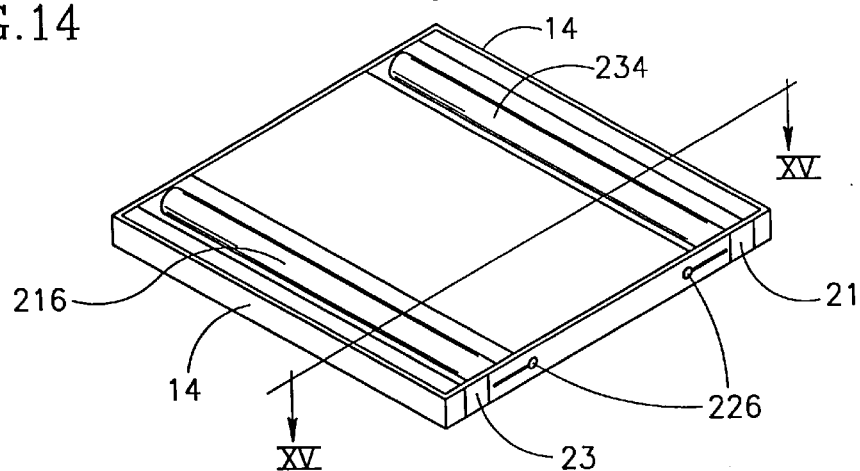
FIG. 15 is a schematic cross section illustration along lines XV—XV in FIG. 14.
Figure 15:
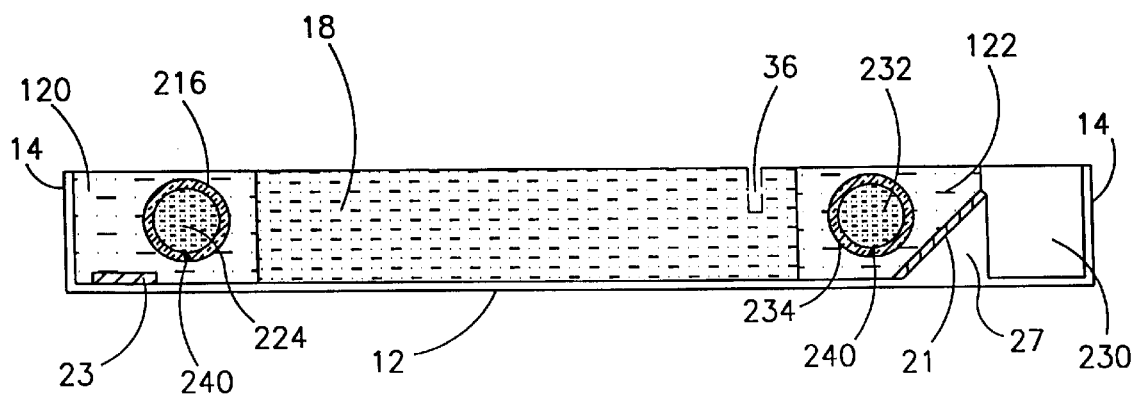

Cassette 225 comprises two ampoules 216 and 234 generally similar to ampoules 116 and 134 which are capable of melting by passing an electric current therethrough. As best seen in FIG. 13, a conducting wire 240 is embedded in the wall of ampoules 216 and 234. In the illustrated embodiment, conducting wire 240 is a high resistivity single wire having two ends 226 to which electric current in a closed circuit may be applied.

In operation, ampoules 216 and 234 are melted just before the electrophoretic test is started by passing a current through conductive wire 240 by connecting an electrical power source to contacts 226. Preferably, the portions of conductive wire 240 not embedded in ampoules 216 and 234 are coated with an insulating material so as to insulate them.

Figure 16:
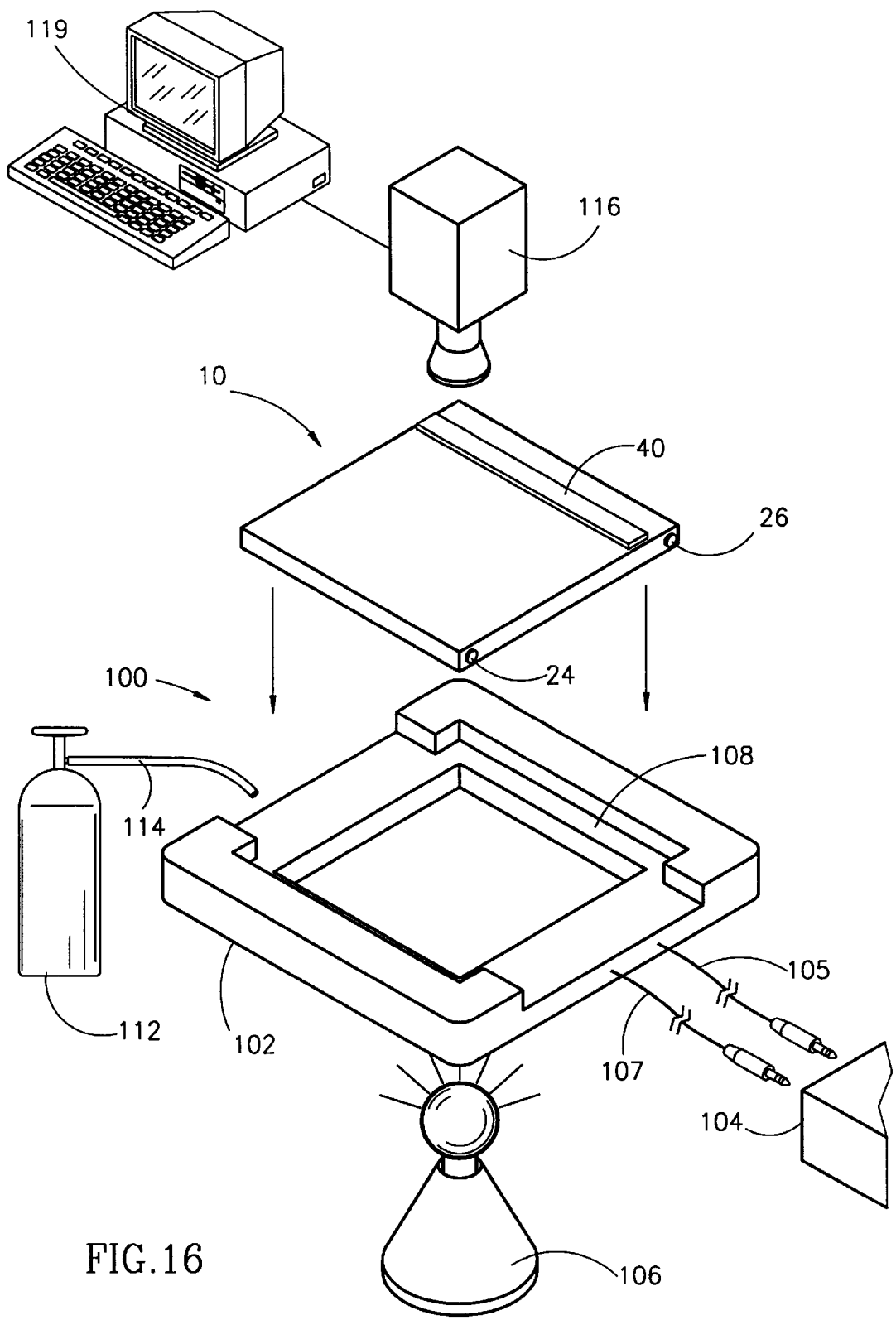
FIG. 16 is schematic isometric illustration of a system for electrophoresis, constructed and operative in accordance with a preferred embodiment of the present invention.

Reference is now made to FIG. 16 which is a schematic isometric illustration of a system for conducting a plurality of electrophoresis tests and which is suitable for visualizing and documenting, in situ, the results thereof, constructed and operative in accordance with a preferred embodiment of the present invention. The system, generally referenced 100, preferably comprises a holder or support housing 102 for supporting any of cassettes 10, 25, 125 or 225, a power supply 104 for providing the direct current (DC) required for driving the electrophoresis separation process, a cable 105 for connecting any of cassettes 10, 25, 125 and 225 to power supply 104 and an ultra violet (UV) light source 106 for illuminating the cassettes 10, 25, 125 or 225.

Holder 102 preferably comprises two contact points (not shown) to which the rods 24 and 26 of the cassette 10, or strips 21 and 23 of cassettes 25,125 or 225 are connected so as to provide thereto the electric field required for the electrophoresis separation.

Optionally, system 100 also comprises a second cable 107 for providing the current required to heat conductive wire 240 in case cassette 225 is used. Accordingly, holder 102 includes an additional pair of contacts to which contacts 226 of cassette 225 are connected so as to provide thereto the electric current required for the heating conductive wire 240.

Another optional feature of system 100 is means for cooling any of cassettes 10, 25, 125, or 225, during the electrophoresis test, such as a flow of cooled gas, for example, liquid nitrogen, schematically illustrated by the balloon 112 and the tube 114.

In a preferred embodiment, system 100 also comprise means for documenting the electrophoresis separation results. In the illustrated embodiment these include a camera, preferably a video camera 116 and a computer 119 operatively connected to camera 116 and executing any suitable application for image analysis of the results of the electrophoresis separation.

It is a particular feature of system 100 that both the electrophoresis test, the visualization of the results thereof and optionally the documentation and the analysis thereof are performed when the cassette is in situ, i.e in holder 102.

Unlike prior art electrophoresis systems for DNA molecules separation where the gel is taken and immersed in a UV sensitive marker, typically ethidium bromide, after the test, cassettes 10, 25, 125 and 225 preferably include ethidium cations as described hereinabove so as to enable the visualization and thus the documentation and analysis of the electrophoresis test results.

In the embodiment illustrated in FIG. 16, the holder 102 is a stand alone open box-like construction which includes a support surface 108 on which any of cassettes 10, 25,125 or 225 is placed. Alternatively, it may include a UV transparent bottom surface.

Another particular feature of the system 100 is that relative to prior art, a smaller number of operations is required from the user in order to conduct an electrophoresis test employing any of cassettes 10, 25,125 or 225. These steps, for electrophoresis separation of DNA molecules, include:

A. A sample which includes the DNA molecules to be separated is introduced in wells;

B. For cassettes 125 and 225 only, ampoules 116 and 134 are broken;

C. The electrical current is switched on;

D. If it is desired to expedite the separation the cooled gas flow is also used;

E. As a result of steps A and C; A, B and C; A, C and D; or A, B, C and D; both electrophoresis separation and interaction of a UV detectable compound with the separated DNA molecules take place at the same time;

F. The UV lamp 106 is turned on to visualize the results of the separation. The results may be also recorded by the video camera 116;

G. The results may be transmitted on line to computer 119 for on the flight quantitative analysis of the electrophoresis test results; and H. The user disposes the cassette 10.

It will be appreciated that the preferred embodiments described hereinabove are described by way of example only and that numerous modifications thereto, all of which fall within the scope of the present invention, exist. For example, any of the cassettes of the present invention may include a combination of the ion exchange matrix disposed at one side of the gel 18 and the closed reservoir disposed at the other end thereof. Another example which is within the scope of the present invention is a two dimensional cassette in which the ion sources are disposed on all four sides of gel 18.

It will be appreciated by persons skilled in the art that the present invention is not limited to what has been particularly shown and described hereinabove. Rather, the scope of the present invention is defined only by the claims that follow:

We claim:

1. Apparatus for conducting electrophoresis separation therein, the apparatus comprising:

a housing having at least bottom and side walls defining a chamber, said chamber comprises, in contact therebetween, prior to said electrophoresis separation:

a body of separating gel for carrying therein said electrophoresis separation;

at least one ion source for providing ions for driving said electrophoresis separation, said at least one ion source having a volume smaller than a volume of said body of gel; and electrodes for connecting said chamber to an external electrical power source, to enable driving said electrophoresis separation.

2. Apparatus according to claim 1 and further comprising a cover for closing said chamber to provide a closed apparatus.

3. Apparatus according to claim 2 wherein said chamber or cover further comprises at least one opening therein for introducing at least one test sample into said body of gel.

4. Apparatus according to claim 2 wherein said cover is transparent to ultra violet (UV) radiation.

5. Apparatus according to claim 2 wherein said cover comprises at least one vent hole which is closed prior to an electrophoresis test and which a user opens just before said electrophoresis test.

6. Apparatus according to claim 1 wherein at least one of said electrodes comprises a strip of conductive material.

7. A substantially closed cassette apparatus for conducting therein electrophoresis separation comprising:
 a substantially closed chamber which comprises therein, prior to said electrophoresis separation:
  a body of separating gel for carrying therein said electrophoresis separation;
  at least one ion source for providing ions for driving said electrophoresis separation, said at least one ion source having a volume smaller than a volume of said body of gel; and
  electrodes for connecting said cassette to an external electrical power source, to enable driving said electrophoresis separation.

8. Apparatus according to claim 1 or 7 wherein said at least one ion source comprises a body of ion exchange matrix.

9. Apparatus according to claim 8 wherein said body of ion exchange matrix comprises:
 a body of cation exchange matrix for providing cations for driving said electrophoresis separation; and
 a body of anion exchange matrix for providing anions for driving said electrophoresis separation.

10. Apparatus according to claim 9 wherein said body of cation exchange matrix is at one end of said gel and said body of anion exchange matrix is on a second end of said body of separating gel.

11. Apparatus according to claim 9 wherein said cation exchange matrix and said anion exchange matrix comprise particles immersed in a support matrix.

12. Apparatus according to claim 11 wherein said support matrix comprises a gel similar to said body of separating gel.

13. Apparatus according to claim 9 further comprising a body of gel of low gel strength, disposed between said chamber and said anion exchange matrix, said body of gel of low gel strength shrinks during said electrophoresis separation to provide a volume in which gases produced at a vicinity of an anode of said chamber accumulate.

14. Apparatus according to claim 9 and further comprising a buffer solution in contact with said body of gel, said at least one of said body of ion exchange matrix and said electrodes.

15. Apparatus according to claim 14 wherein said buffer is a solution tris-acetate ethylendiamine tetra acetic acid buffer solution, said cation exchange matrix releases Tris cations and said anion exchange matrix releases acetate anions.

16. Apparatus according to claim 9 wherein said cation exchange matrix further comprises ethidium cations.

17. Apparatus according to claim 7 wherein said chamber further comprises at least one opening therein for introducing a test sample into said body of gel.

18. Apparatus according to claim 17 or 3 further comprising a comb which closes said at least one opening prior to the electrophoresis separation.

19. Apparatus according to claim 1 or 7 wherein said chamber is transparent to ultra violet (UV) radiation.

20. Apparatus according to claim 7 wherein said chamber comprises at least one vent hole which is closed prior to an electrophoresis test and which a user opens just before said electrophoresis test.

21. Apparatus according to claim 1 or 7 wherein said apparatus is generally flat.

22. Apparatus according to claim 1 or 7 wherein said apparatus is disposable.

23. Apparatus according to claim 1 or 7 wherein at least one of said electrodes comprises a conductive material for adsorbing at least part of at least one gas produced during said electrophoresis separation.

24. Apparatus according to claim 23 wherein said at least one of said electrodes comprises a material selected from the group consisting of aluminum, palladium, an alloy containing aluminum and an alloy containing palladium.

25. Apparatus according to claim 24 wherein said gases include oxygen created at a vicinity of one of said electrodes operating as an anode during said electrophoresis separation and reacting with said aluminum.

26. Apparatus according to claim 24 wherein said gases include hydrogen created at a vicinity of one of said electrodes operating as a cathode during said electrophoresis separation and wherein said hydrogen is adsorbed by said palladium.

27. Apparatus according to claim 1 or 7 further comprising means enabling visualization of said electrophoresis separation.

28. Apparatus for conducting electrophoresis separation therein, the apparatus comprising:
 a housing having at least bottom and side walls defining a chamber, said chamber comprises, therein;
 a body of gel for carrying therein said electrophoresis separation;
 at least one ion source for providing ions for driving said electrophoresis, separation said at least one ion source having a volume smaller than a volume of said body of gel: and
 electrodes for connecting said chamber to an external electrical power source, to enable driving said electrophoresis separation,
 wherein said at least one ion source comprises a closed reservoir having therein a buffer solution having higher concentration than a concentration of a buffer solution of said body of gel for carrying therein said electrophoresis separation, said closed reservoir being opened just before said electrophoresis separation for providing said ions for driving said electrophoresis separation.

29. Apparatus according to claim 28 wherein said closed reservoir is a breakable ampoule.

30. Apparatus according to claim 29 wherein said breakable ampoule is surrounded by a space, said space at least partially filled with said buffer solution in a concentration generally similar to that of said body of gel for carrying therein said electrophoresis separation.

31. Apparatus according to claim 28 wherein said buffer solution is a tris-acetate ethylendiamine tetra acetic acid buffer solution.

32. Apparatus according to claim 28 wherein said closed reservoir having therein said buffer solution also comprising ethidium cations.

33. An electrophoresis method comprising the steps of:
introducing at least one test sample into a body of gel;
applying an electrical field to said body of gel; and
driving an electrophoresis separation by providing ions required for driving said electrophoresis separation by at least one ion source having a volume smaller than a volume of said gel.

34. A method for producing a generally closed cassette for conducting electrophoresis separation therein comprising:
providing a housing having bottom and side walls defining an open chamber;
assembling within said chamber therein a body of gel for carrying therein said electrophoresis separation, at least one ion source for providing ions for driving said electrophoresis separation, said at least one ion source having a volume smaller than a volume of said body of gel and electrodes for connecting said chamber to an external electrical power source; and
closing said open housing with a cover, to form a generally closed cassette for carrying said electrophoresis separation therein.

35. A closed cassette apparatus for conducting therein electrophoresis separation comprising:
a closed chamber which comprises therein:
a body of gel for carrying therein said electrophoresis separation;
at least one ion source for providing ions for driving said electrophoresis separation; and
electrodes for connecting said cassette apparatus to an external electrical power source, to enable driving said electrophoresis separation,
wherein said at least one ion source comprises a closed reservoir having therein a buffer solution having higher concentration than a concentration of a buffer solution of said body of gel for carrying therein said electrophoresis separation, said closed reservoir which a user opens just before said electrophoresis separation for providing said ions for driving said electrophoresis separation;
and wherein said closed reservoir is a breakable ampoule.

36. Apparatus according to claim 35 wherein said buffer solution is a tris-acetate ethylendiamine tetra buffer solution.

37. Apparatus according to claim 35 wherein said buffer also comprises ethidium cations.

38. Apparatus for conducting electrophoresis separation therein, the apparatus comprising:
a housing having at least bottom and side walls defining a chamber, said chamber comprises therein:
a body of gel for carrying therein said electrophoresis separation;
at least one ion source for providing ions for driving said electrophoresis separation, said at least one ion source having a volume smaller than a volume of said body of gel; and
electrodes for connecting said chamber to an external electrical power source, to enable driving said electrophoresis separation,
wherein at least one of said electrodes comprises a strip of conductive material mounted on a ramp, said ramp being inclined at an angle relative to said bottom wall, to direct gases produced at the vicinity of said step during said electrophoresis separation to an empty volume receiving said gases.

39. A substantially closed cassette for conducting therein electrophoresis separation comprising:
a substantially closed chamber which comprises therein:
a body of gel for carrying therein said electrophoresis separation;
at least one ion source for providing ions for driving said electrophoresis separation; and
electrodes for connecting said chamber to an external electrical power source, to enable driving said electrophoresis separation,
wherein at least one of said electrodes comprises a strip of conductive material mounted on a ramp, said ramp being inclined at an angle relative to a bottom wall of said closed chamber, to direct gases produced at a vicinity of said strip during said electrophoresis separation to an empty volume receiving said gases.

40. Apparatus for conducting electrophoresis separation therein, the apparatus comprising:
a housing having at least bottom and side walls defining a chamber, said chamber comprises therein:
a body of gel for carrying therein said electrophoresis separation;
at least one ion source for providing ions for driving said electrophoresis separation, said at least one ion source having a volume smaller than a volume of said body Of gel;
electrodes for connecting said chamber to an external electrical power source, to enable driving said electrophoresis separation;
wherein said chamber further includes at least one empty volume for accumulating gases produced during said electrophoresis separation.

41. A substantially closed cassette for conducting therein electrophoresis separation comprising:
a substantially closed chamber which comprises therein:
a body of gel for carrying therein said electrophoresis separation;
at least one ion source for providing ions for driving said electrophoresis separation; and
electrodes for connecting said chamber to an external electrical power source, to enable driving said electrophoresis separation,
wherein said closed chamber further includes at least one empty volume for accumulating gases produced during said electrophoresis separation.

* * * * *